(12) United States Patent
Ducote, Jr. et al.

(10) Patent No.: US 11,543,181 B2
(45) Date of Patent: Jan. 3, 2023

(54) DEHYDROGENATION SEPARATION UNIT WITH MIXED REFRIGERANT COOLING

(71) Applicant: Chart Energy & Chemicals, Inc., Ball Ground, GA (US)

(72) Inventors: Douglas A. Ducote, Jr., The Woodlands, TX (US); Brent A. Heyrman, The Woodlands, TX (US); Timothy P. Gushanas, Pearland, TX (US); Richard Hopewell, The Woodlands, TX (US)

(73) Assignee: Chart Energy & Chemicals, Inc., Ball Ground, GA (US)

( * ) Notice: Subject to any disclaimer, the term of this patent is extended or adjusted under 35 U.S.C. 154(b) by 472 days.

(21) Appl. No.: 16/595,866

(22) Filed: Oct. 8, 2019

(65) Prior Publication Data

US 2020/0109893 A1 Apr. 9, 2020

Related U.S. Application Data

(60) Provisional application No. 62/743,263, filed on Oct. 9, 2018.

(51) Int. Cl.
*F25J 3/00* (2006.01)
*C07C 7/09* (2006.01)
(Continued)

(52) U.S. Cl.
CPC .............. *F25J 3/0655* (2013.01); *C07C 7/09* (2013.01); *F25J 1/0022* (2013.01); *F25J 3/0645* (2013.01);
(Continued)

(58) Field of Classification Search
CPC ........ F25J 3/00; F25J 3/06; F25J 3/065; F25J 3/0645; F25J 3/0655; F25J 3/0209;
(Continued)

(56) References Cited

U.S. PATENT DOCUMENTS 4,072,485 A * 2/1978 Becdelievre ............. F25J 3/064
62/612
4,217,759 A 8/1980 Shenoy
(Continued)

FOREIGN PATENT DOCUMENTS

CN 1509262 A 6/2004
CN 203187601 U 9/2013
(Continued)

OTHER PUBLICATIONS

Invitation to Pay Additional Fees And, Where Applicable, Protest Fee by the International Search Authority for International Application No. PCT/US2019/055170, dated Jan. 8, 2020, (16 pages).
(Continued)

*Primary Examiner* — Miguel A Diaz
*Assistant Examiner* — Erik Mendoza-Wilkenfel
(74) *Attorney, Agent, or Firm* — Cook Alex Ltd.

(57) ABSTRACT

A system for separating olefinic hydrocarbon and hydrogen in an effluent fluid stream from a dehydrogenation reactor includes a heat exchanger that receives and partially condenses the effluent fluid stream so that a mixed phase effluent stream is formed. A primary separation device receives and separates the mixed phase effluent stream into a primary vapor stream and a primary liquid product stream. A heat exchanger receives and partially condenses the primary vapor stream so that a mixed phase primary stream is formed. A secondary separation device receives and separates the mixed phase primary stream into a secondary vapor stream and a secondary liquid product stream. A heat exchanger receives and warms the secondary vapor stream to provide refrigeration for partially condensing the effluent fluid stream and a heat exchanger receives and warms the secondary vapor stream to provide refrigeration for partially condensing the primary vapor stream. A mixed refrigerant
(Continued)

compression system provides refrigerant to a heat exchanger to provide refrigeration.

16 Claims, 5 Drawing Sheets

(51) Int. Cl.
*F25J 3/06* (2006.01)
*F25J 1/00* (2006.01)

(52) U.S. Cl.
CPC ........ *F25J 2205/40* (2013.01); *F25J 2205/82* (2013.01); *F25J 2210/06* (2013.01); *F25J 2210/12* (2013.01); *F25J 2210/60* (2013.01); *F25J 2230/20* (2013.01); *F25J 2230/30* (2013.01); *F25J 2240/02* (2013.01); *F25J 2245/02* (2013.01); *F25J 2270/66* (2013.01)

(58) Field of Classification Search
CPC ........ F25J 3/0214; F25J 3/0204; F25J 3/0252; F25J 2205/40; F25J 2205/82; F25J 2210/06; F25J 2210/12; F25J 2210/60; F25J 2230/20; F25J 2230/30; F25J 2240/02; F25J 2245/02; F25J 2270/66; F25J 1/00; F25J 1/0022; F25J 1/0047; F25J 1/005; F25J 1/0052; F25J 1/006; F25J 1/008; F25J 1/0085; F25J 1/0087; F25J 1/0092; F25J 1/0211; F25J 1/0212; C07C 7/09
See application file for complete search history.

(56) References Cited

U.S. PATENT DOCUMENTS

| | | | |
|---|---|---|---|
| 4,707,170 | A | 11/1987 | Ayres et al. |
| 4,738,699 | A * | 4/1988 | Apffel .................... F25J 3/0257 62/623 |
| 4,921,514 | A | 5/1990 | Rowles et al. |
| 5,262,034 | A | 11/1993 | Kunz et al. |
| 5,329,774 | A * | 7/1994 | Tanguay .................. C07C 7/09 62/612 |
| 5,657,643 | A | 8/1997 | Price |
| 5,746,066 | A | 5/1998 | Manley |
| 6,333,445 | B1 | 12/2001 | O'Brien |
| 6,560,989 | B1 | 5/2003 | Roberts et al. |
| 6,581,409 | B2 | 6/2003 | Wilding et al. |
| 6,637,237 | B1 | 10/2003 | Wei et al. |
| 6,705,113 | B2 | 3/2004 | Wei et al. |
| 7,065,974 | B2 | 6/2006 | Grenfell |
| 7,082,787 | B2 | 8/2006 | Lee et al. |
| 7,278,264 | B2 | 10/2007 | Brostow |
| 7,437,891 | B2 | 10/2008 | Reyneke et al. |
| 8,013,201 | B2 | 9/2011 | Panditrao |
| 8,563,793 | B2 | 10/2013 | Zimmermann et al. |
| 9,574,822 | B2 | 2/2017 | Haberberger et al. |
| 9,746,234 | B2 | 8/2017 | Byfield et al. |
| 2002/0174679 | A1 | 11/2002 | Wei |
| 2006/0149115 | A1 | 7/2006 | Foral et al. |
| 2007/0208432 | A1 | 9/2007 | Hawrysz |
| 2010/0186929 | A1 | 7/2010 | Chantant et al. |
| 2010/0217059 | A1 | 8/2010 | Reyneke et al. |
| 2010/0281915 | A1 | 11/2010 | Roberts et al. |
| 2011/0146342 | A1 | 6/2011 | Sumner |
| 2011/0226008 | A1 | 9/2011 | Gushanas et al. |
| 2014/0260415 | A1 | 9/2014 | Ducote et al. |
| 2015/0260451 | A1 | 9/2015 | Haberberger et al. |
| 2015/0329445 | A1 | 11/2015 | Kleiber et al. |
| 2017/0010043 | A1 | 1/2017 | Ducote, Jr. et al. |
| 2018/0087832 | A1 | 3/2018 | Roberts et al. |
| 2019/0194094 | A1 | 6/2019 | Jo et al. |

FOREIGN PATENT DOCUMENTS

| | | |
|---|---|---|
| DE | 10110462 A | 9/2002 |
| WO | 2019194094 A1 | 10/2019 |
| WO | 2022008095 A1 | 1/2022 |

OTHER PUBLICATIONS

Bauer, Heinz, "Cryogenic Olefins Recovery From Dehydrogenation Reactor Effluents", AICHE Symposium on Cryogenic Gas Processing 1992 Spring National Meeting, Linde AG Munich, Germany, Jan. 1992.

Mafi, et al.,'Development in Mixed Refrigerant Cycles Used in Olefin Plants', Proceedings of the 1st Annual Gas Processing Symposium, Elsevier, vol. 1, 2009.

Barclay, et al., Enhanced Single Mixed Refrigerant Process For Stranded Gas Liquefaction, pp. 1-10.

Chinese First Office Action for Application No. 201980066720.9 dated Aug. 9, 2022.

Chinese Search Report for Chinese Application No. 20198006672098 dated Aug. 9, 2022.

* cited by examiner

DEHYDROGENATION SEPARATION UNIT WITH MIXED REFRIGERANT COOLING

CLAIM OF PRIORITY

This application claims the benefit of U.S. Provisional Application No. 62/743,263, filed Oct. 9, 2018, the contents of which are hereby incorporated by reference.

BACKGROUND OF THE INVENTION

Propane Dehydrogenation (PDH) Separation Systems are known in the art. An example of such a system is described in commonly owned U.S. Pat. No. 6,333,445, the contents of which are incorporated herein by reference.

The current designs for PDH separation systems requires that the Reactor Effluent vapor stream be compressed to high pressure (~12 Barg) using the Reactor Effluent Compressor and then de-pressurized using two, generator-loaded or compressor-loaded, cryogenic turbo-expanders to provide the refrigeration required for the separation and recovery of the liquid olefin product.

Disadvantages of such prior art systems include power consumption of the overall process, the added cost and maintenance requirements of the turbo-expander/generator (or compressor) sets, the high required Reactor Effluent Compressor discharge pressure (which increases capital and operating costs) and lack of flexibility to significantly adjust the olefin and hydrogen separation temperatures.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for separating olefinic hydrocarbon and hydrogen in an effluent fluid stream from a dehydrogenation reactor includes a main heat exchanger configured to receive and partially condense the effluent fluid stream so that a mixed phase effluent stream is formed. A primary separation device is in fluid communication with the main heat exchanger so as to receive and separate the mixed phase effluent stream into a primary vapor stream and a primary liquid product stream. The main heat exchanger configured to receive and partially condense the primary vapor stream so that a mixed phase primary stream is formed. A secondary separation device is in fluid communication with the main heat exchanger so as to receive and separate the mixed phase primary stream into a secondary vapor stream and a secondary liquid product stream. The main heat exchanger is configured to receive and warm the secondary vapor stream to provide refrigeration for partially condensing the effluent fluid stream and the primary vapor stream. A mixed refrigerant compression system is configured to also provide refrigerant to the main heat exchanger.

In another aspect, a system for separating olefinic hydrocarbon and hydrogen in an effluent fluid stream from a dehydrogenation reactor includes a cold box feed heat exchanger configured to receive and partially condense the effluent fluid stream so that a mixed phase effluent stream is formed. A primary separation device is in fluid communication with the cold box feed heat exchanger so as to receive and separate the mixed phase effluent stream into a primary vapor stream and a primary liquid product stream. A mixed refrigerant heat exchanger is configured to receive and partially condense the primary vapor stream so that a mixed phase primary stream is formed. A secondary separation device is in fluid communication with the mixed refrigerant heat exchanger so as to receive and separate the mixed phase primary stream into a secondary vapor stream and a secondary liquid product stream. The mixed refrigerant heat exchanger is configured to receive and warm the secondary vapor stream to provide refrigeration for partially condensing the primary vapor stream. The cold box feed heat exchanger is configured to receive and further warm the secondary vapor stream after exiting the mixed refrigerant heat exchanger to provide refrigeration for partially condensing the effluent fluid stream. A mixed refrigerant compression system is configured to provide refrigerant to the mixed refrigerant heat exchanger.

In still another aspect, a method for separating olefinic hydrocarbon and hydrogen in an effluent fluid stream from a dehydrogenation reactor includes the steps of partially condensing the effluent fluid stream so that a mixed phase effluent stream is formed, separating the mixed phase effluent stream into a primary vapor stream and a primary liquid product stream, partially condensing the primary vapor stream so that a mixed phase primary stream is formed, separating the mixed phase primary stream into a secondary vapor stream and a secondary liquid product stream, warming the secondary vapor stream to provide refrigeration for partially condensing the effluent fluid stream and the primary vapor stream and providing refrigerant to the main heat exchanger from a mixed refrigerant compression system.

DETAILED DESCRIPTION OF EMBODIMENTS

The present invention is a dehydrogenation separation unit that here uses a Mixed Refrigerant (MR) system, consisting of a MR compressor with heat exchangers and drums, to provide the refrigeration required for the separation and recovery of the liquid olefin product. As examples only, the MR system can either use a single mixed refrigerant system or be a single mixed refrigerant system that is pre-cooled using a second refrigerant.

While achieving the same product recovery as prior art systems, some of the benefits may include: 1) the power consumption of the overall process is lower, 2) both turbo-expander/generator (or compressor) sets are eliminated, 3) the required Reactor Effluent Compressor discharge pressure is significantly reduced, which saves capital and operating costs, 4) the operation, maintenance and reliability of the Separation System is improved with the MR process compared to the turbo-expander process, 5) the MR process allows for a more robust and forgiving design of the main Feed Heat Exchanger, 6) the MR process provides an independent means to adjust the refrigeration level for the Separation System without impacting the Recycle Effluent Compressor.

Since propylene refrigeration is used in many PDH facilities, the MR process described herein uses propylene refrigeration to pre-cool the MR refrigerant and reduce the MR compressor power consumption. Pre-cooling also allows the MR component mix to be simplified, requiring only methane, ethylene (or ethane) and propylene (or propane), with ethylene and propylene being preferred. Without $C_4$ or $C_5$ in the MR mix, the possibility of reactor catalyst contamination is reduced.

While the explanation of the invention presented below is specific to a Propane Dehydrogenation Unit, the same process may be employed for Butane Dehydrogenation.

Figure 1:
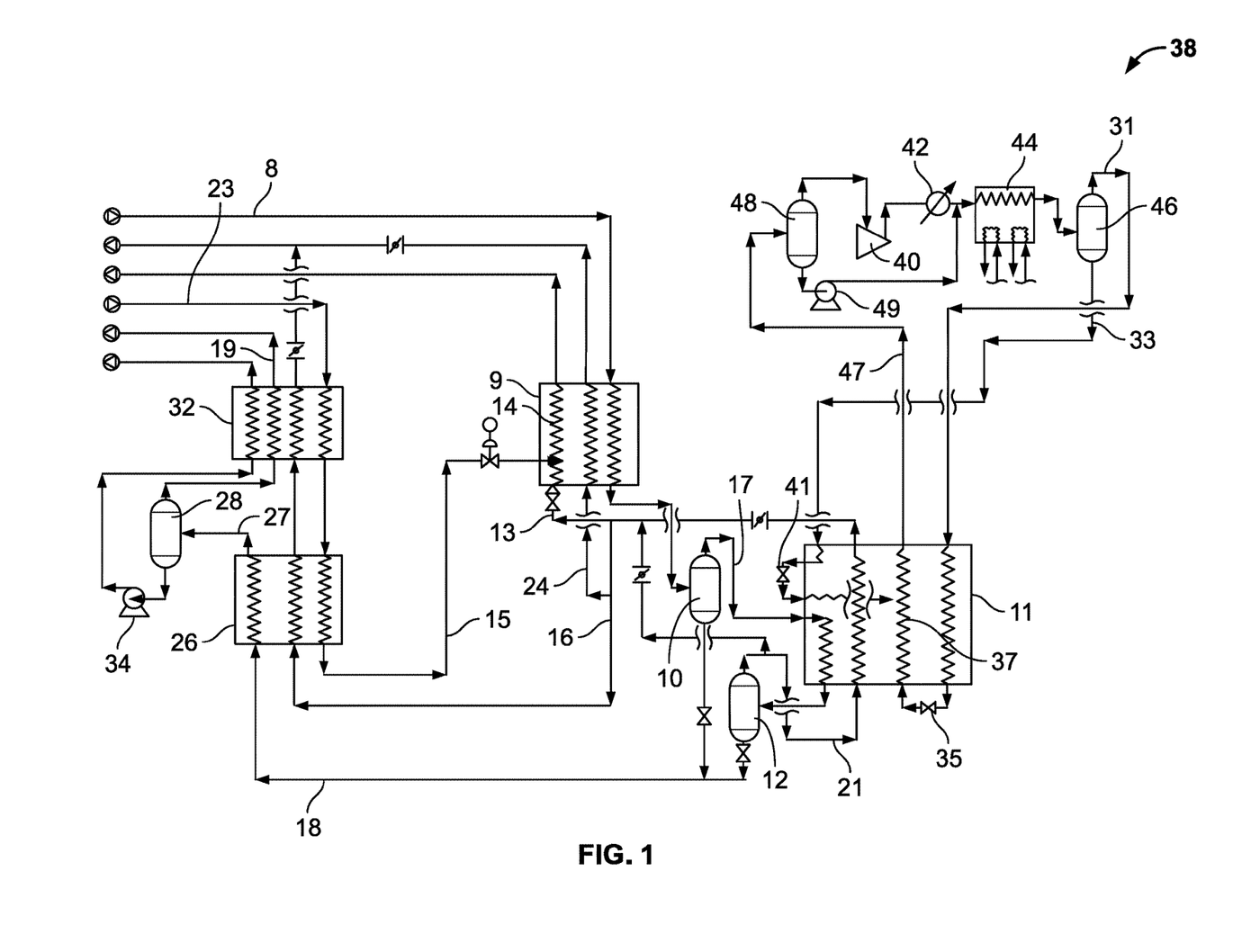
FIG. 1 is a schematic of a first embodiment of the system of the disclosure.

With reference to FIG. 1, Reactor Effluent Gas is compressed in the REC compressor to ~7.2 Barg and the heat of compression is removed prior to entering the cryogenic Separation System as the Cold Box Vapor Feed 8. The gas is sent to the Cold Box Feed Heat Exchanger 9, where it is partially condensed and then flows to an outlet Primary Separator 10. Vapor and liquid are separated, with the liquid stream containing a portion of the $C_3$ olefin product and a vapor stream 17 containing hydrogen and the remaining olefin product.

This vapor steam 17 flows to the Mixed Refrigerant Heat Exchanger 11 (MR exchanger), where it is further cooled to the required temperature and partially condensed to achieve the desired product recovery. The partially condensed stream flows to the Secondary Separator 12 and is separated into a liquid olefin product and a hydrogen rich vapor stream 21. The hydrogen rich stream is reheated in the MR exchanger and is then divided into two streams—Recycle Gas 13 (which is the hydrogen required for the Combined Reactor Feed) and Net Vapor 16, which is the balance of the hydrogen stream and which will be exported from the Separation System.

The Net Vapor stream is reheated and refrigeration recovered in a Fresh Feed Heat Exchanger (having cold end 26 and warm end 32). The liquid product streams (from the Primary and Secondary Separators 10 and 12) are combined for form combined liquid product stream 18 and flow to the Fresh Feed Heat Exchanger 26, 32.

The Cold Box Vapor Feed 8 ("Reactor Effluent") is cooled firstly in the Cold Box Feed Exchanger. It is cooled primarily by the Combined Reactor Feed 14 and secondarily by a portion 24 of the export Net Vapor Product 16. The Combined Reactor Feed provides the bulk of the refrigeration, by combining the Recycle Gas stream 13 with a cold Fresh Feed liquid stream 15 (such as propane or n-butane) and vaporizing the combined stream in the Cold Box Feed Heat Exchanger 9. The cold Fresh Feed liquid stream 15 is formed from a Fresh Feed inlet stream 23 that is sub-cooled in the Fresh Feed Heat Exchanger at 26 and 32, before entering the Cold Box Feed Heat Exchanger 9. Refrigeration for the Fresh Feed is provided by recovering the cold from the C3 olefin product 18 and from a portion of the Net Vapor Product 16.

Flash Gas (recycle) 19 is produced by partially warming the separator liquids in the cold-end section 26 of the Fresh Feed Exchanger. The resulting vapor-liquid mix 27 is separated in the Liquid Product Tank 28. The vapor from tank 28 is warmed in the warm-end section 32 of the Fresh Feed Exchanger and the Flash Gas 19 is recycled to the suction of the upstream Reactor Effluent Compressor (see FIG. 1 of U.S. Pat. No. 6,333,445). The Liquid Product from tank 28 is pumped via pump 34 and additional cold is recovered in the warm-end section 32 of the Fresh Feed Exchanger.

The overall refrigeration balance for the Separation System is provided by the Mixed Refrigerant (MR) compression system, indicated in general at 38 in FIG. 1, via the final cooling in the MR Exchanger (MRHX) 11. A $C_3$ pre-cooled MR system is described here; however, a single MR system may also be used. FIG. 1 shows a single-stage MR Compressor 40, followed by an air or water cooler 42, and then followed by a $C_3$ (propylene) pre-cooler 44. The pre-cooler can utilize as many stages of refrigeration as required to obtain the desired temperature, two stages are shown for simplicity. The MR refrigerant is separated via separator 46 into vapor and liquid phase streams 31 and 33, respectively, and sent to the MRHX 11. The MR vapor stream 31 is cooled and condensed in the MRHX 11 and is flashed at 35 to create the coldest refrigerant for the process and the low pressure refrigerant stream 37. The MR liquid stream 33 is also cooled in the MRHX, flashed at 41 and sent to the low pressure refrigerant stream 37, where it joins and is mixed with the low pressure refrigerant stream 37 at a warmer temperature. The common refrigerant return stream 47 exits the MRHX as a mixed phase vapor/liquid stream. Before being compressed, the vapor and liquid are separated via separator 48. The liquid is pumped via pump 49 to higher pressure and the vapor is compressed at compressor 40 to the required discharge pressure. The system uses a typical MR composition suitable for the specific design conditions.

The heat exchangers illustrated in FIG. 1 and described above may be incorporated or integrated into a single main heat exchanger.

Figure 2:
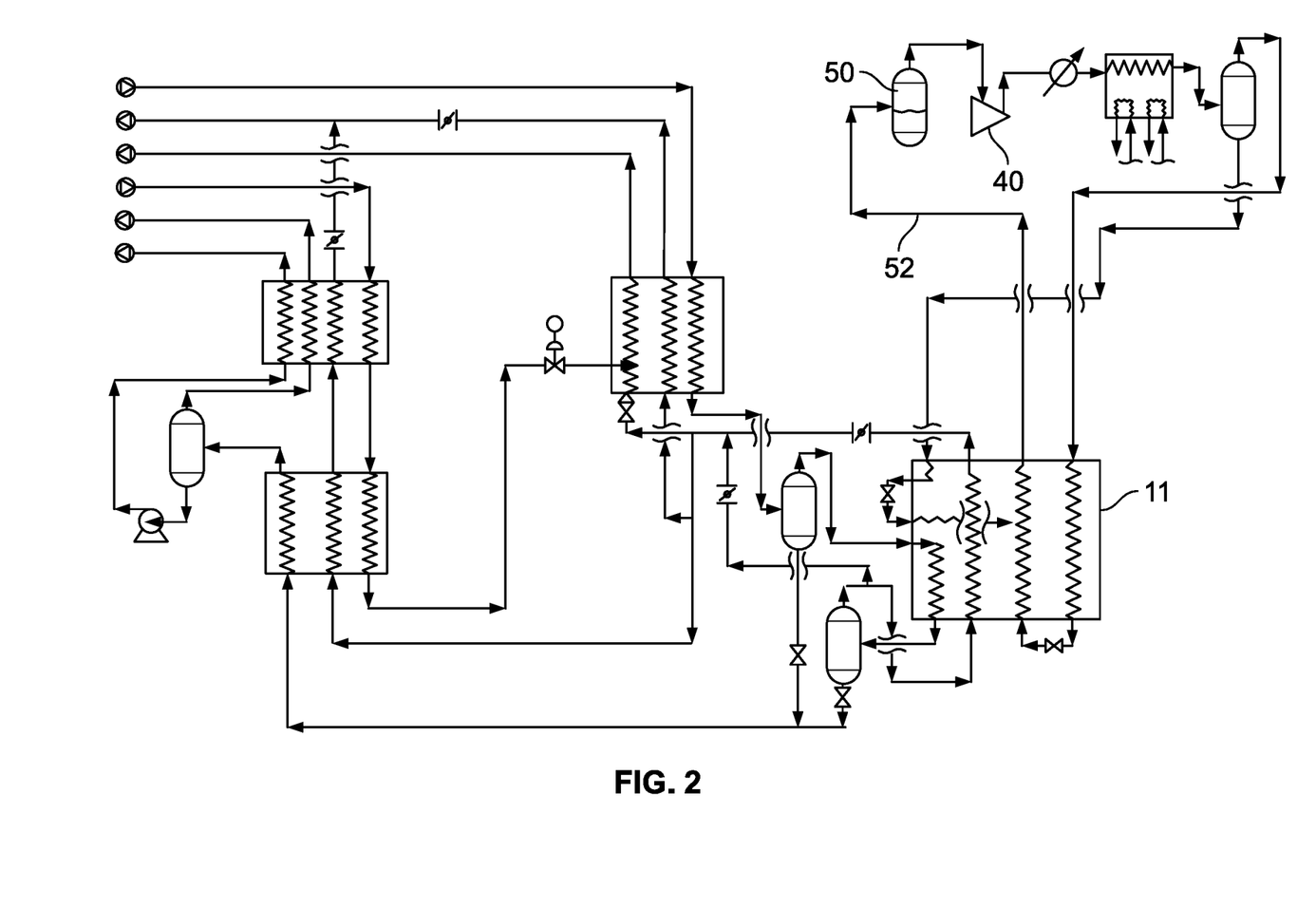
FIG. 2 is a schematic of a second embodiment of the system of the disclosure.

With reference to FIG. 2, in a second embodiment of the system, the suction drum to the MR Compressor can also be designed to act as a heavy component refrigerant accumulator. The MR system may be operated with excess heavy components (such as $C_3$, $C_4$ or $C_5$) in the refrigerant and with the resulting MR being, at least temporarily, a 2-phase stream 52 exiting the exchanger 11. These excess heavy components are separated in the compressor suction drum 50 and remain in the drum. The refrigerant vapor, which flows to the MR Compressor 40, is now at its dew point and the system operates automatically at the dew point condition. As "make up" refrigerant is added to the system, the accumulated heavy components will then equilibrate with light components to the dew point at suction pressure and temperature. If needed, the heavy components can be preferentially removed from the refrigeration system at the suction accumulator or preferentially added and retained in the suction drum.

Figure 3:
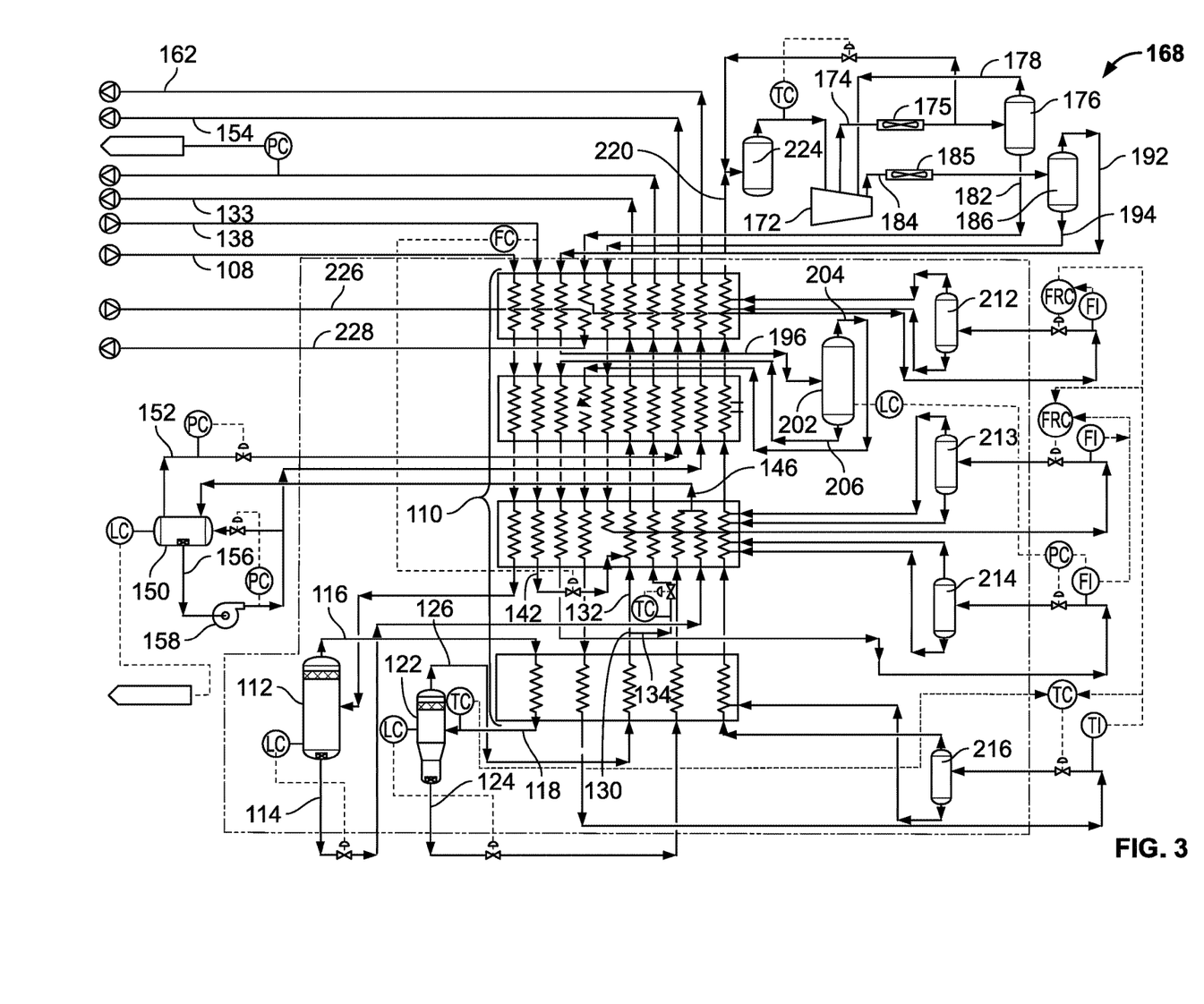
FIG. 3 is a schematic of a third embodiment of the system of the disclosure.

In a third embodiment of the system, illustrated in FIG. 3, Reactor Effluent Gas is compressed in the REC compressor to ~7.2 Barg and the heat of compression is removed via ambient exchanger (air or water) cooling prior to entering the Cryogenic Separation System as the Cold Box Vapor Feed 108. The gas is sent to the Main Heat Exchanger 110, where it is cooled and partially condensed and then flows to the Primary Separator 112. Vapor and liquid are separated, with the liquid stream 114 containing a portion of the C3 olefin product and the vapor stream 116 containing hydrogen and the remaining olefin product. This vapor steam flows back to the Main Heat Exchanger 110, where it is further cooled and partially condensed to achieve the desired product recovery. The partially condensed stream 118 flows to the Secondary Separator 122 and is separated into a liquid olefin product 124 and a hydrogen rich stream 126. The hydrogen rich vapor stream is reheated in the Main Heat Exchanger and is then divided at 130 into two streams—Recycle Gas 132 (which is the hydrogen required for the Combined Reactor Feed 133) and Net Vapor 134 (which is the remaining balance of the hydrogen stream and will be exported from the Separation System). The Net Vapor stream is reheated and the refrigeration is recovered in the Main Heat Exchanger.

Warm fresh propane feed 138 is sent to the Main Heat Exchanger 110, and cooled to the same temperature as the Primary Separator 112. The cooled fresh propane feed 142 is then mixed with the Recycle Gas 132 to form the Combined Reactor Feed 133. This stream is reheated, and the refrigeration is recovered in the Main Heat Exchanger. This provides the majority of the refrigeration for the cryogenic separation system.

The liquid product streams 114 and 124 (from the Primary and Secondary Separators 112 and 122) are fed to the Main Heat Exchanger 110 at an appropriate location relative to their respective temperature. The liquid product streams are heated, and partially vaporized. The liquid product streams exit the Main Heat Exchanger thru a common header to form liquid product stream 146. This orientation of the liquid product streams improves efficiency, reduces piping complexity, and lowers the risk of freezing.

The partially vaporized mixed C3 liquid product stream 146 is sent to the Liquid Product Tank 150. The vapor 152 from the Liquid Product Tank (Flash Gas) is heated in the Main Heat Exchanger and then recycled to the suction of the upstream Reactor Effluent Compressor as Flash Gas Stream 154. The liquid 156 from the Liquid Product Tank (Liquid Product) is pumped via pump 158, and then heated in the Main Heat Exchanger for additional energy recovery. The warmed Liquid Product exits the Main Heat Exchanger as C3 Product stream 162.

The overall refrigeration balance for the Separation System is provided by a Mixed Refrigerant (MR) system, indicated in general at 168. The embodiment of FIG. 3 uses a two-stage MR Compressor 172, with air or water intercooling and discharge cooling. The discharge 174 of the first MR Compressor Stage is partially condensed at 175, and sent to the MR Interstage Drum 176. The vapor 178 is sent to the Second MR Compressor Stage, and the liquid 182 is sent to the Main Heat Exchanger 110. The second MR Compressor Stage Discharge 184 is partially condensed at 185, and separated in the MR Accumulator 186. The MR Accumulator Vapor 192 and Liquid 194 are sent to the Main Heat Exchanger 110. The MR Accumulator Vapor is partially condensed in the Main Heat Exchanger, and the resulting stream 196 is sent to a Cold Vapor Separator Drum 202 in order to improve the process efficiency. The Cold Vapor Separator Vapor 204, Cold Vapor Separator Liquid 206, MR Accumulator Liquid 194, and MR Interstage Liquid 182 are all condensed and subcooled in the Main Heat Exchanger 110. All of these streams exit the exchanger, are flashed across JT Valves (as an example only), and the resulting mixed phase streams separated and sent back to the Main Heat Exchanger via standpipes 212, 213, 214 and 216 at the appropriate temperatures to provide the refrigeration balance required for the separation system. Additional details regarding operation of the MR system 168 are available in commonly owned U.S. Patent Appl. Publ. No. US 2014/0260415 to Ducote, Jr. et al., the entire contents of which are hereby incorporated by reference.

The flashed low pressure MR streams are mixed within the Main Heat Exchanger and exit as a single superheated vapor stream 220 which is sent to the MR Compressor Suction Drum 224. The system uses a typical MR composition suitable for the specific design conditions.

The MR system allows for the integration of additional heat transfer services that are at ambient temperature or cooler into the Main Heat Exchanger. As an example, FIG. 3 shows the integration of the Deethanizer Rectifier Condenser (deethanizer overhead inlet stream 226 and deethanizer overhead outlet stream 228) into the Main Heat Exchanger. This increases the size of the MR system due to the additional refrigeration duty that is required, but removes the need for a separate C3 refrigeration system for the Deethanizer Rectifier Condenser service which reduces overall equipment count for the dehydrogenation plant.

Figure 4:
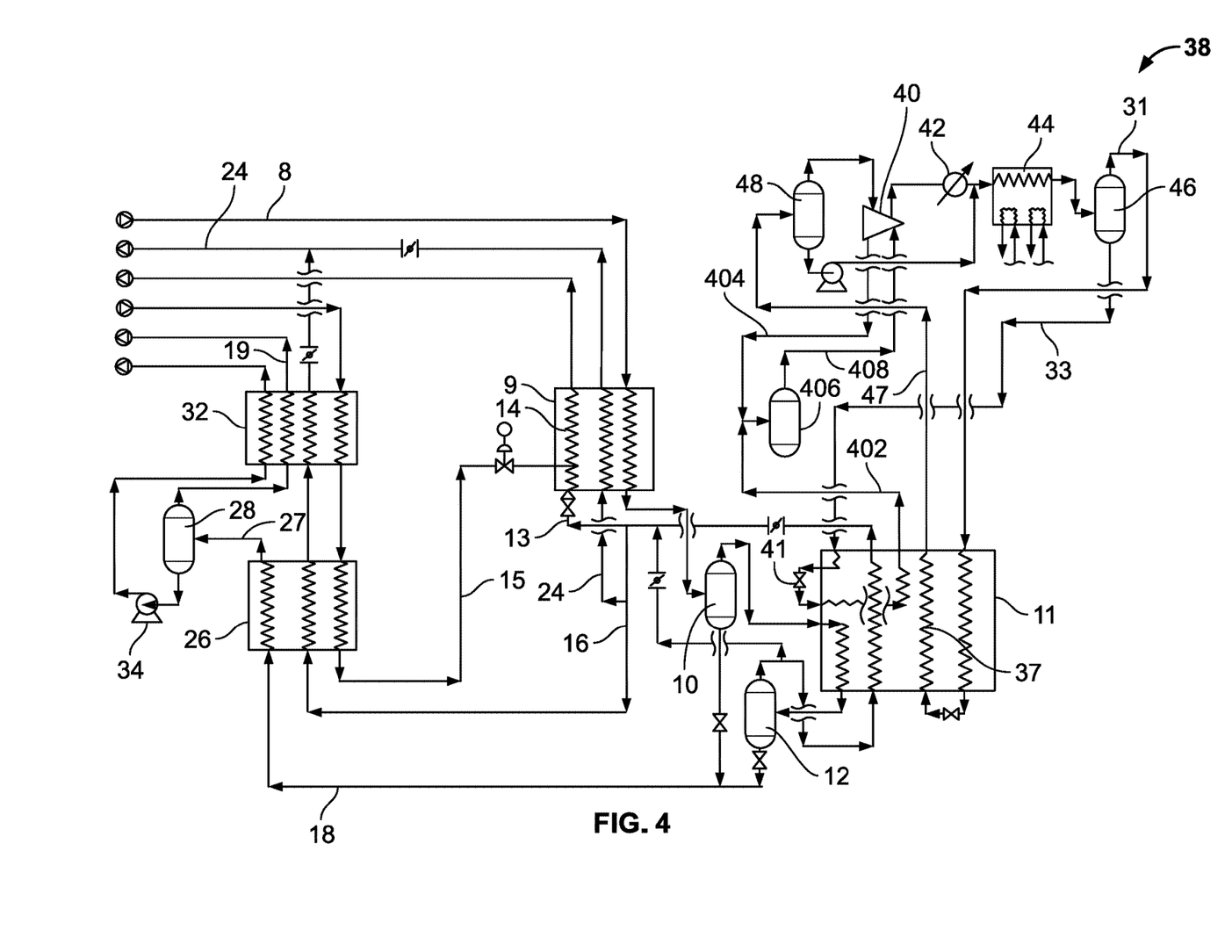
FIG. 4 is a schematic of a fourth embodiment of the system of the disclosure.

In a fourth embodiment of the system of the disclosure, illustrated in FIG. 4, an interstage separation device 406 is added to the system of FIG. 1. A mixed phase MR stream 402, from MR heat exchanger 11 (which originated as the liquid outlet of separator 46 prior to entering the MR heat exchanger), is combined with a mixed phase MR stream 404 from the outlet of the first stage of compressor 40. The combined stream is directed to the inlet of separation device 406 and the resulting vapor stream 408 is directed into the inlet of the second stage of compressor 40. The outlet of the second stage of compressor 40 is directed to cooling devices 42 and 44, and processing of the MR stream then continues as described above with respect to FIG. 1, with the exception that stream 33, after cooling in mixed refrigerant heat exchanger 11 and flashing via valve 41, does not join with the low pressure refrigerant stream 37. In alternative embodiments, however, a portion of the stream 33, after cooling in mixed refrigerant heat exchanger 11 and flashing via valve 41, may join the low pressure refrigerant stream 37.

Figure 5:
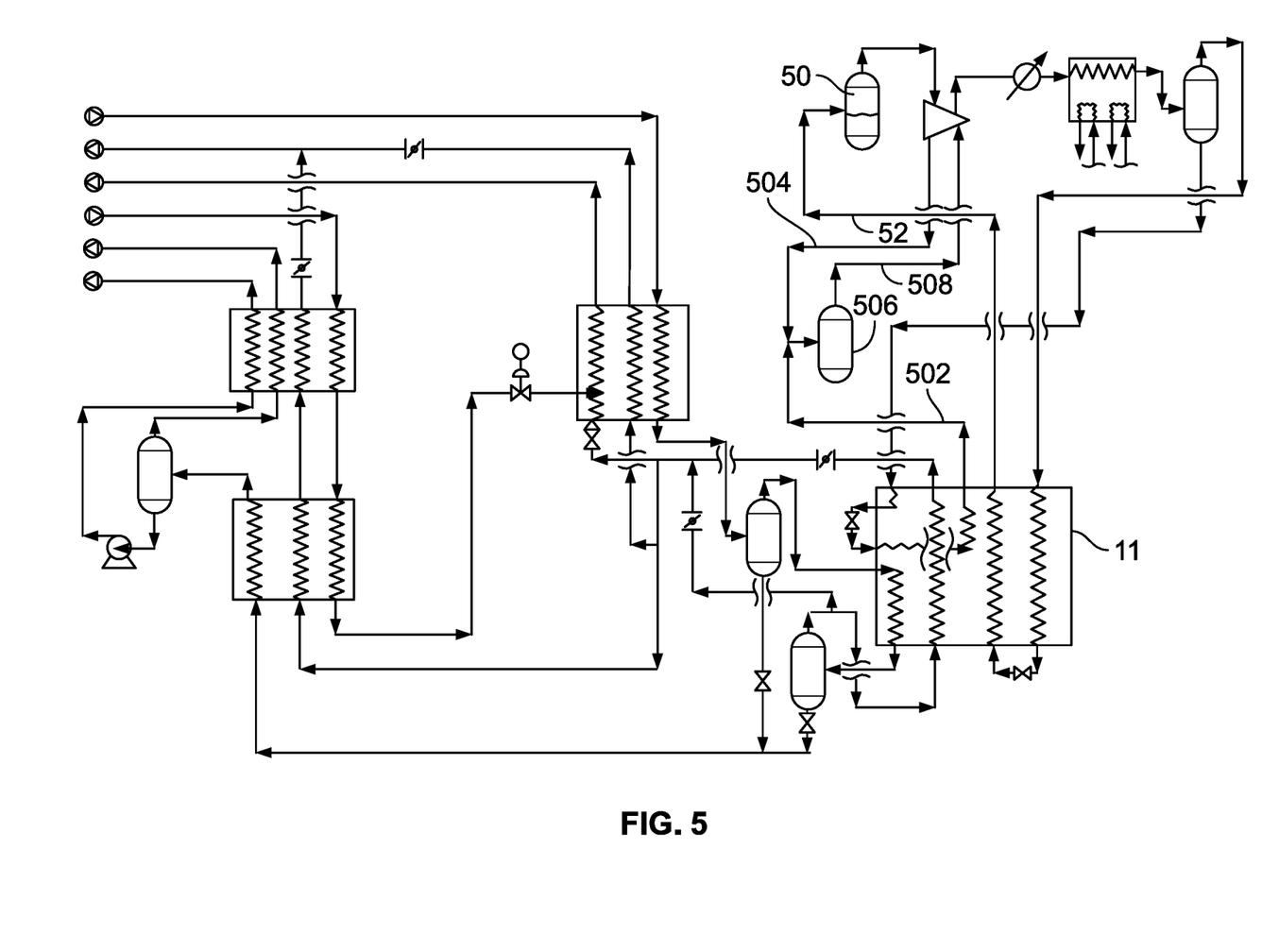
FIG. 5 is a schematic of a fifth embodiment of the system of the disclosure.

In a fifth embodiment of the system of the disclosure, illustrated in FIG. 5, an interstage separation device 506 is added to the system of FIG. 2. A mixed phase MR stream 502, from MR heat exchanger 11, is combined with a mixed phase MR stream 504 from the outlet of the first stage of a MR compressor. The combined stream is directed to the inlet of separation device 506 and the resulting vapor stream 508 is directed into the inlet of the second stage of the MR compressor. The outlet of the second stage of the MR compressor is directed to one or more cooling devices, and processing of the MR stream then continues as described above with respect to FIG. 4.

The referenced heat exchangers in the description may be combined, with the use of multi-stream heat exchangers, such as Brazed Aluminum Plate Fin heat exchangers, to simplify the piping design, plant layout or performance. Examples of combinations may be the Fresh Feed-1 Exchanger with the Fresh Feed-2 Exchangers or both Fresh Feed Exchangers with the Cold Box Feed Exchanger. Other combinations may also be desirable.

While the preferred embodiments of the invention have been shown and described, it will be apparent to those skilled in the art that changes and modifications may be made therein without departing from the scope of the invention.

What is claimed is:

1. A system for separating olefinic hydrocarbon and hydrogen in an effluent fluid stream from a dehydrogenation reactor comprising:
   a. a main heat exchanger configured to receive and partially condense the effluent fluid stream so that a mixed phase effluent stream is formed;
   b. a primary separation device in fluid communication with the main heat exchanger so as to receive and separate the mixed phase effluent stream into a primary vapor stream and a primary liquid product stream;

c. said main heat exchanger configured to receive and partially condense the primary vapor stream so that a mixed phase primary stream is formed;

d. a secondary separation device in fluid communication with the main heat exchanger so as to receive and separate the mixed phase primary stream into a secondary vapor stream and a secondary liquid product stream;

e. said main heat exchanger configured to receive and warm the secondary vapor stream to provide refrigeration for partially condensing the effluent fluid stream and the primary vapor stream;

f. a mixed refrigerant compression system configured to provide refrigerant to the main heat exchanger;

g. a junction configured to receive and combine the primary and secondary liquid product streams from the primary and secondary separation devices so that a combined liquid product stream is formed;

h. said main heat exchanger including a fresh feed cooling passage that is configured to receive and cool a fresh feed stream and a liquid product passage that is configured to receive and warm the combined liquid product stream so that refrigeration is provided to the fresh feed cooling passage, said fresh feed cooling passage having an outlet configured so that a cooled fresh feed stream is directed to and joins the secondary vapor stream.

2. The system of claim 1 wherein the main heat exchanger includes a primary refrigeration passage and the mixed refrigerant compression system includes:

i) a suction separation device configured to receive a mixed phase refrigerant stream from the primary refrigeration passage of the main heat exchanger;

ii) a compressor having an inlet in fluid communication with the suction separation device;

iii) a cooling device having an inlet in fluid communication with an outlet of the compressor;

iv) a accumulator having an inlet in fluid communication with an outlet of the cooling device and liquid and vapor outlets in fluid communication with the primary refrigeration passage of the main heat exchanger.

3. The system of claim 2 wherein the cooling device includes an air or water cooler followed by a propylene pre-cooler.

4. The system of claim 2 wherein the main heat exchanger is configured to partially condense a vapor stream from the vapor outlet of the accumulator to form a mixed phase accumulator stream and further comprising a cold vapor separator having an inlet configured to receive the mixed phase accumulator stream, said cold vapor separator having a vapor outlet and a liquid outlet in fluid communication with the primary refrigeration passage of the heat exchanger.

5. The system of claim 4 wherein the mixed refrigerant compression system includes:

i) an interstage separation device having an inlet in fluid communication with the cooling device, a liquid outlet in fluid communication with the primary refrigeration passage of the heat exchanger and a vapor outlet;

ii) a compressor second stage having an inlet in fluid communication with the vapor outlet of the interstage separation device;

iii) a second stage cooling device having an inlet in fluid communication with an outlet of the compressor and an outlet in fluid communication with the accumulator.

6. The system of claim 5 wherein the compressor is a two-stage compressor including a first stage having an inlet in fluid communication with an outlet of the suction separation device and an outlet in fluid communication with the cooling device, and a second stage having an inlet in fluid communication with the interstage separation device and an outlet in fluid communication with the second stage cooling device.

7. The system of claim 1 wherein the fresh feed stream includes primarily propane or primarily n-butane.

8. The system of claim 1 wherein the main heat exchanger includes a cold box feed heat exchanger configured to receive and partially condense the effluent feed stream using refrigeration from the secondary vapor stream, a mixed refrigerant heat exchanger configured to receive and cool the primary vapor stream using refrigerant from the mixed refrigerant compression system and a fresh feed heat exchanger configured to receive and cool the fresh feed stream using refrigeration from the combined liquid product stream.

9. A system for separating olefinic hydrocarbon and hydrogen in an effluent fluid stream from a dehydrogenation reactor comprising:

a. a cold box feed heat exchanger configured to receive and partially condense the effluent fluid stream so that a mixed phase effluent stream is formed;

b. a primary separation device in fluid communication with the cold box feed heat exchanger so as to receive and separate the mixed phase effluent stream into a primary vapor stream and a primary liquid product stream;

c. a mixed refrigerant heat exchanger configured to receive and partially condense the primary vapor stream so that a mixed phase primary stream is formed;

d. a secondary separation device in fluid communication with the mixed refrigerant heat exchanger so as to receive and separate the mixed phase primary stream into a secondary vapor stream and a secondary liquid product stream;

e. said mixed refrigerant heat exchanger configured to receive and warm the secondary vapor stream to provide refrigeration for partially condensing the primary vapor stream;

f. said cold box feed heat exchanger configured to receive and further warm the secondary vapor stream after exiting the mixed refrigerant heat exchanger to provide refrigeration for partially condensing the effluent fluid stream;

g. a mixed refrigerant compression system configured to provide refrigerant to the mixed refrigerant heat exchanger;

h. a junction configured to receive and combine the primary and secondary liquid product streams from the primary and secondary separation devices so that a combined liquid product stream is formed;

i. a fresh feed heat exchanger including a fresh feed cooling passage that is configured to receive and cool a fresh feed stream and a liquid product passage that is configured to receive and warm the combined liquid product stream so that refrigeration is provided to the fresh feed cooling passage, said fresh feed cooling passage having an outlet configured so that a cooled fresh feed stream is directed to and joins the secondary vapor stream prior to entering the cold box feed heat exchanger.

10. The system of claim 9 wherein the mixed refrigerant heat exchanger includes a primary refrigeration passage and the mixed refrigerant compression system includes:
  i) a suction separation device configured to receive a mixed phase refrigerant stream from the primary refrigeration passage of the mixed refrigerant heat exchanger;
  ii) a compressor having an inlet in fluid communication with the suction separation device;
  iii) a cooling device having an inlet in fluid communication with an outlet of the compressor;
  iv) a accumulator having an inlet in fluid communication with an outlet of the cooling device and liquid and vapor outlets in fluid communication with the primary refrigeration passage of the mixed refrigerant heat exchanger.

11. The system of claim 10 wherein the cooling device includes an air or water cooler followed by a propylene pre-cooler.

12. The system of claim 10 wherein the suction separation device includes a vapor outlet in fluid communication with an inlet of the compressor and a liquid outlet and further comprising a pump having pump inlet in fluid communication with the liquid outlet of the suction separation device and a pump outlet in fluid communication with the outlet of the cooling device.

13. The system of claim 12 further comprising an interstage separation device and wherein the compressor is a two-stage compressor including a first stage and a second stage, wherein the first stage has an inlet in fluid communication with the vapor outlet of the suction separation device and an outlet in fluid communication an inlet of the interstage separation device, and wherein the second stage has an inlet in fluid communication with an outlet of the interstage separation device and an outlet in fluid communication with the cooling device and wherein the inlet of the interstage separation device is also in fluid communication with the liquid outlet of the accumulator.

14. The system of claim 10 further comprising an interstage separation device and wherein the compressor is a two-stage compressor including a first stage and a second stage, wherein the first stage has an inlet in fluid communication with the vapor outlet of the suction separation device and an outlet in fluid communication an inlet of the interstage separation device, and wherein the second stage has an inlet in fluid communication with an outlet of the interstage separation device and an outlet in fluid communication with the cooling device and wherein the inlet of the interstage separation device is also in fluid communication with the liquid outlet of the accumulator.

15. The system of claim 9 wherein the fresh feed stream includes primarily propane or primarily n-butane.

16. The system of claim 9 wherein the cold box feed heat exchanger, the mixed refrigerant heat exchanger and the fresh feed heat exchanger are incorporated within a main heat exchanger.

* * * * *